United States Patent [19]

Wang et al.

[11] 4,073,820
[45] Feb. 14, 1978

[54] OLEFIN METATHESIS PROCESS

[75] Inventors: Jin-Liang Wang; Melvin Brown, both of Akron; Henry R. Menapace, Stow, all of Ohio

[73] Assignee: The Goodyear Tire & Rubber Company, Akron, Ohio

[21] Appl. No.: 740,902

[22] Filed: Nov. 11, 1976

Related U.S. Application Data

[63] Continuation of Ser. No. 584,244, June 5, 1975, abandoned, which is a continuation of Ser. No. 252,178, May 11, 1972, abandoned, which is a continuation-in-part of Ser. No. 99,258, Dec. 17, 1970, abandoned.

[51] Int. Cl.² .................................................. C07C 3/62
[52] U.S. Cl. .................................................. 260/683 D
[58] Field of Search .................................... 260/683 D

[56] References Cited

U.S. PATENT DOCUMENTS 2,951,066   8/1960   Coover et al. .................... 252/429 B

*Primary Examiner*—Delbert E. Gantz
*Assistant Examiner*—C. E. Spresser
*Attorney, Agent, or Firm*—F. W. Brunner; J. Y. Clowney

[57] ABSTRACT

There is disclosed an olefin metathesis process which comprises subjecting at least one olefin to a catalyst system consisting of (1) salts of the metals selected from the group of tungsten, molybdenum and chromium, said salts being halides or the reaction products of these metal halides with carboxylic acids, phenols and 1,3-diketones, (2) a material selected from the group represented by the formulae:

$$R_{3-n}MX_n$$

and $$R_3M_2X_3$$

wherein R is an alkyl radical containing from 1 to 12 carbon atoms, M is selected from the group consisting of aluminum, gallium and indium, X is a halogen from the group of fluorine, chlorine, bromine and iodine, and $n$ equals 0, 1 or 2, and (3) a compound defined by the formula:

$$N R_1 R_2 R_3$$

in which $R_1$ and $R_2$ are selected from the group of hydrogen, alkyl, aralkyl, aryl, alkenyl and alkaryl, $R_3$ is selected from the group of hydrogen, alkyl and alkenyl, said R's containing from 1 to 20 carbon atoms, to produce olefins containing a higher or lower number of carbon atoms than the original olefins.

2 Claims, No Drawings

OLEFIN METATHESIS PROCESS

This is a continuation of application Ser. No. 584,244, filed June 5, 1975, which is a continuation of application Ser. No. 252,178, filed May 11, 1972, which was a continuation-in-part of application Ser. No. 99,258, filed Dec. 17, 1970, all now abandoned.

This invention is directed to an olefin metathesis process or an olefin disporportionation process. It is directed to a process whereby olefins are converted into other olefins having a higher or lower number of carbon atoms than the original olefin.

For example, which is not to be construed to be the limit of the invention, 2-pentene can be converted into an olefin containing a higher number of carbon atoms such as 3-hexene and an olefin containing a lower number of carbon atoms such as 2-butene:

| 2-pentene | $H_3C-HC=CH-CH_2-CH_3$ |
| --- | --- |
| 2-butene | $H_3C-CH=CH-CH_3$ |
| | + |
| 3-hexene | $H_3C-CH_2-CH=CH-CH_2-CH_3$ |

According to the invention, olefins are contacted with a catalyst comprising (1) certain salts of the metals tungsten, molybdenum and chromium, said salts being halides, the reaction products of these metal halides with phenols, the reaction products of these metal halides with carboxylic acids and the reaction products of these metal halides with 1,3-diketones, (2) a material selected from the group represented by the formulae:

$$R_{3-n}MX_n$$

and $$R_3M_2X_3$$

wherein R is an alkyl radical containing from 1 to 12 carbon atoms, M is selected from the group of aluminum, gallium and indium and X is a halogen from the group of fluorine, chlorine, bromine and iodine and $n$ is 0, 1 or 2, and (3) a compound defined by the formula:

$$N R_1R_2R_3$$

in which $R_1$ and $R_2$ are selected from the group of hydrogen, alkyl, aralkyl, aryl, alkenyl and alkaryl, $R_3$ is selected from the group of hydrogen, alkyl and alkenyl containing up to 20 carbon atoms.

The first component of the catalyst useful in this invention are certain derivatives of tungsten, molybdenum and chromium. Among these metal derivatives are the halides, such as the chlorides, the bromides, the iodides and the fluorides. Representative, but not exhaustive, of such metal halides are tungsten hexachloride, tungsten pentachloride, tungsten pentabromide, tungsten pentaiodide, molybdenum pentachloride, molybdenum pentabromide, molybdenum pentaiodide, chromium trichloride, chromium trifluoride, chromium tribromide and chromium triiodide. Also useful are the reaction products of these metal halides with phenols, carboxylic acids and diketones. Representative of such compounds are phenol, 2-methylphenol, 2-bromophenol, 4-chlorophenol, salicylaldehyde, 2-acetophenol, 2-benzoylphenol, salicylic acid, methyl salicylate, n-butyl salicylate, benzoic acid, monomethyl phthalate, 2-ethyl hexanoic acid, neodecanoic acid, 2,4-pentadione, 1,5-hexamethyl-2,4-pentadione, dibenzoyl menthane and the like. Representative of the compounds formed when these materials are reacted with tungsten, molybdenum or chromium halides are bis-acetatotetrachloro tungsten, bis-acetatotetrabromo tungsten, acetatopentachloro tungsten, acetatopentabromo tungsten, 2-ethylhexanatopentachloro tungsten, neodecanatopentachloro tungsten, 2-carbomethoxyphenoxypentachloro tungsten, 2-carbomethoxyphenoxytetrachloro tungsten, phenoxypentachloro tungsten, bis-phenoxypentachloro tungsten, 2-acetylphenoxypentachloro tungsten, 2,5-pentanedionatopentachloro tungsten, 2,2,6,6-tetramethylheptane-3,5-dionatopentachloro tungsten and the like.

The second component of the catalyst useful in this invention may be represented by the formulae:

$$R_{3-n}MX_n$$

and $$R_3M_2X_3$$

wherein R is an alkyl radical containing from 1 to 12 carbon atoms, M is selected from the group of aluminum, gallium and indium and X is a halogen from the group of fluorine, chlorine, bromine and iodine and $n$ may be 0, 1 or 2. Representative of such compounds are the various trialkyl aluminum compounds such as triethylaluminum, triisobutylaluminum tridodecylaluminum and the like, and the aluminum sesqui halides, representative of which are ethylaluminum sesquichloride, ethylaluminum sesquibromide and other alkyl aluminum compounds in which the alkyl radicals contain up to 12 carbon atoms and also other alkyl aluminum halides containing the other halides, bromides, iodides and fluorides.

The third component of the catalyst may be represented by the formula:

$$N R_1R_2R_3$$

wherein $R_1$ and $R_2$ are selected from the group of hydrogen, alkyl, aralkyl, aryl, alkenyl and alkaryl, $R_3$ is selected from the group of hydrogen, alkyl and alkenyl and $R_1$, $R_2$ and $R_3$ contain from 1 to 20 carbon atoms.

The hydrogen atoms of the carbon atoms of these compounds may be mono- or di-substituted by various groups such as halogen, alkyl, alkoxy, dialkyl, amino, nitro, cyano, carboxy, carboalkoxy, acetoxy and trihalomethyl, in any combination. Representative of such compounds are ammonia, n-butylamine, diethylamine, cyclohexylamine, 2-pentenylamine, cyclohexenylamine, aniline, n-methylaniline, diphenylamine, 2-, 3-, or 4-haloanilines, 2-, 3-, or 4-alkylanilines, triethylamine, 2,4,6-trichloroaniline, 2,4,6-tribromoaniline, 2,3,4,5,6-pentafluoroaniline, 2-, 3-, or 4-methoxyaniline, 2-, 3-, or 4-nitroaniline, 2-, 3-, or 4-cyanoaniline, 2-, 3-, or 4-carboxyaniline, 2-, 3-, or 4-carbomethoxyaniline, 2-, 3-, or 4-acetoxyaniline, 4-trifluoromethylaniline, 2,6-dimethyl-4-bromoaniline, 4-dimethylaminoaniline and other compounds wherein the R's are substituted as set forth above.

The olefins which may be metathesized in accordance with this invention may range from those olefins containing 3 carbon atoms up to 20 or 30 carbon atoms. This is not to say, however, that ethylene cannot enter into a metathesis reaction if it is in mixture with another olefin containing a higher number of carbon atoms. One could readily observe that ethylene alone could only rearrange itself to form ethylene again when undergoing metathesis.

The temperatures at which the olefin metathesis reaction takes place are extremely mild and may range from extremely low temperatures such as −20° C. up to 100° C. or more. However, one of the many advantages of this invention is that olefins may be metathesized at ambient temperature. Likewise, the pressures employed in this process may be ambient pressures, however, this does not rule out the use of subatmospheric or superatmospheric pressures.

This process may be carried out in the presence of only the olefins. On the other hand, an inert catalyst may be employed, if desired. Any solvent in which the olefins are soluble may be used so long as the solvent does not deactivate the catalyst.

The molar relationships among the catalyst components is not terribly critical. For instance, the mole ratio of the nitrogen ligand to the salts of tungsten, molybdenum and chromium may range from 0.5/1 to 3.0/1 with 1.0/1 to 2.0/1 being preferred. The molar relationship of the metal alkyl compound to the tungsten, molybdenum or chromium salts may range from about 0.5/1 to about 5.0/1 with 1.0/1 to 3.0/1 being preferred.

It has been observed that the amount of catalyst employed in this invention may also vary quite widely. For instance, based on the metal salt of W, Mo or Cr as unity, the mole ratio of the reactant olefin may vary broadly from about 10/1 to about 3000/1 with about 50/1 to about 500/1 being more preferred. Amount of olefin to catalyst levels above 300/1 will cause metathesis to occur but at very slow rates.

The catalyst may be employed as in situ catalyst systems or preformed catalyst systems. By the term "in situ" is meant that each individual catalyst component is added to a reactor individually which contains the olefin to be metathesized and any inert solvent, if desired, and allowed to react with each other in the presence of the olefin to form the catalyst. By the term "preformed" is meant that the catalyst components which are to be used are mixed prior to contact with the olefin and added to the reactor as a prepared catalyst. The catalyst components are usually dissolved in an inert solvent to facilitate more accurate measurements. Suitable examples of inert solvents are benzene, chlorobenzene and the like.

Further amplification of this invention may be had by the following examples which are intended to be representative rather than restrictive of the scope of the invention.

EXAMPLE I

To a 4-ounce bottle was added 0.0002 mole of tungsten hexachloride, 0.0003 mole of aniline and 0.0002 mole of ethylaluminum sesquichloride, each dissolved in small amounts of an inert hydrocarbon, chlorobenzene. To the bottle containing the catalyst was added 0.02 mole of propylene to 40 cc of chlorobenzene as an inert solvent. This mixture was allowed to react for 60 minutes at 25° C. At the end of this time, the catalyst was deactivated with the addition of 1 milliliter of isopropanol. An analysis by vapor phase chromatography indicated that 28 percent of the propylene had been converted to other olefins, namely, ethylene and 2-butene, and the selectivity of the combined ethylene and 2-butene was 100 percent, indicating that no other olefins were produced except ethylene and 2-butene from the propylene which underwent reaction.

EXAMPLE II

An experiment was carried out identical to that of Example I except that the ethylaluminum sesquichloride was replaced by 0.0002 mole of ethylaluminum dichloride. Analysis indicated that 21 percent of the propylene had been converted into other olefins. The combined weight percent selectivity to ethylene and 2-butene was 79 percent.

EXAMPLE III

Another experiment, identical to that of Example I, except the aniline was omitted, was conducted for comparative purposes. Analysis showed that 99 percent of the propylene was converted but that no ethylene or butene had been formed. Apparently, the propylene had been reacted in a manner to form a low molecular weight polypropylene rather than metathesized to a different olefin.

EXAMPLE IV

An experiment was conducted identical to that of Example I except that the aniline was replaced by 0.0003 mole of ethanol. Analysis showed that 99 percent of the propylene was converted with no significant amount of ethylene or butene being formed. Again, the propylene was converted to a low molecular weight polypropylene.

EXAMPLE V

To a 4-ounce bottle was added 0.0002 mole of 2-carbomethoxyphenoxypentachloro tungsten, 0.0002 mole of aniline and 0.0002 mole of ethylaluminum sesquichloride. To this catalyst system was added 0.02 mole of propylene in 40 cc of chlorobenzene. After 60 minutes of reaction at 25° C., the activity of the catalyst was destroyed by the addition of 1 milliliter of isopropanol. Analysis by vapor phase chromatography indicated that 24 percent of the propylene had been converted to other olefins, namely ethylene and 2-butene, which when combined, indicated a weight percent selectivity of 96 percent.

EXAMPLE VI

To a suitable reactor was added 0.7 gram of n-pentene containing 0.7 gram (0.01 mole) of 2-pentene. To this reactor there was added 0.0794 gram (0.0002 mole) of tungsten hexachloride, 0.0362 gram (0.0004 mole) of aniline and 0.024 gram (0.0002 mole) of ethylaluminum sesquichloride. The reactor was shaken for a period of 60 minutes at 25° C. The reaction was terminated by the addition of 1 milliliter of isopropanol. When analyzed by vapor phase gas chromatography, the results indicated that 22 percent of the 2-pentene had been converted in the reaction. The results showed that 50 mole percent of 2-butene and 50 mole percent of 3-hexene had been produced.

EXAMPLE VII

To a 4-ounce bottle was added 0.0002 mole of tungsten hexachloride, 0.0003 mole of aniline and 0.0003 mole of ethylaluminum sesquichloride, all in small amounts in chlorobenzene. To this catalyst was added 0.01 mole of 2-pentene. After 60 minutes at 25° C., the reaction was stopped with the addition of 1 milliliter of isopropanol. Analysis indicated that 50 percent of 2- pentene had been converted with a 53 mole percent selectivity to 3-hexene and a 44 mole percent selectivity to 2-butene.

While certain representative embodiments and details have been shown for the purpose of illustrating the invention, it will be apparent to those skilled in this art that various changes and modifications may be made therein without departing from the spirit or scope of the invention.

What is claimed is:

1. An olefin metathesis process which comprises forming olefins containing a higher number of carbon atoms and a lower number of carbon atoms and the same number of double bonds per olefin than the original olefin feed, by subjecting at least one olefin feed to a catalyst system consisting of
   1. tungsten halides or the reaction product of these tungsten halides with carboxylic acid, phenols and 1,3-diketones,
   2. a material selected from the group represented by the formulae:

$R_{3-n}AlX_n$ and $R_3Al_2X_3$ wherein R is an alkyl radical containing from 1 to 12 carbon atoms, Al is aluminum, X is a halogen from the group of fluorine, chlorine, bromine and iodine, and $n$ equals 0, 1 or 2, and
   3. a compound defined by the formula:

$N R_1R_2R_3$ in which $R_1$ and $R_2$ are selected from the group of hydrogen, alkyl, aralkyl, aryl, alkenyl and alkaryl, $R_3$ is selected from the group of hydrogen, alkyl and alkenyl, said R's containing from 1 to 20 carbon atoms to produce olefins containing a higher and lower number of carbon atoms than the original olefins, in which the molar relationship of catalyst component (3) to catalyst component (1) ranges from 0.5/1 to 3.0/1 and the molar relationship of catalyst component (2) to catalyst component (1) ranges from 0.5/1 to 5.0/1.

2. A process according to claim 1 in which the catalyst component (1) is tungsten hexachloride, catalyst component (2) is an aluminum alkyl chloride and catalyst component (3) is aniline.

* * * * *

UNITED STATES PATENT OFFICE
CERTIFICATE OF CORRECTION

PATENT NO. : 4,073,820

DATED : February 14, 1978

INVENTOR(S) : Jin-Liang Wang, Melvin Brown, Henry R. Menapace

It is certified that error appears in the above-identified patent and that said Letters Patent are hereby corrected as shown below:

Column 3, line 33, "300/1" should be --3000/1--.

Signed and Sealed this

Twenty-sixth Day of June 1984

[SEAL]

Attest:

GERALD J. MOSSINGHOFF

Attesting Officer

Commissioner of Patents and Trademarks